(12) United States Patent
Drescher et al.

(10) Patent No.: US 9,157,865 B2
(45) Date of Patent: Oct. 13, 2015

(54) MACHINE TOOL—BASED, OPTICAL COORDINATE MEASURING MACHINE CALIBRATION DEVICE

(75) Inventors: Joseph D. Drescher, Middletown, CT (US); Erik M. Pedersen, Cheshire, CT (US)

(73) Assignee: United Technologies Corporation, Hartford, CT (US)

( * ) Notice: Subject to any disclaimer, the term of this patent is extended or adjusted under 35 U.S.C. 154(b) by 682 days.

(21) Appl. No.: 13/406,013

(22) Filed: Feb. 27, 2012

(65) Prior Publication Data

US 2012/0188380 A1 Jul. 26, 2012

Related U.S. Application Data

(63) Continuation-in-part of application No. 12/772,510, filed on May 3, 2010, now Pat. No. 8,797,398.

(51) Int. Cl.
| | |
|---|---|
| *H04N 9/47* | (2006.01) |
| *H04N 7/18* | (2006.01) |
| *G01B 5/00* | (2006.01) |
| *G01B 5/004* | (2006.01) |
| *G01B 5/20* | (2006.01) |
| *B23Q 16/00* | (2006.01) |
| *G01B 1/00* | (2006.01) |
| *G01B 3/14* | (2006.01) |
| *B23Q 3/00* | (2006.01) |
| *B25B 1/00* | (2006.01) |
| *B25B 1/20* | (2006.01) |
| *G01C 17/38* | (2006.01) |
| *G01N 21/88* | (2006.01) |
| *G06T 7/00* | (2006.01) |
| *G01B 11/00* | (2006.01) |
| *G01B 11/30* | (2006.01) |
| *G01B 11/02* | (2006.01) |
| *G01B 11/24* | (2006.01) |
| *G01B 11/03* | (2006.01) |
| *G01B 11/25* | (2006.01) |
| *G01N 21/93* | (2006.01) |
| *G01N 21/956* | (2006.01) |

(52) U.S. Cl.
CPC ............ *G01N 21/8806* (2013.01); *G01B 11/00* (2013.01); *G01B 11/022* (2013.01); *G01B 11/026* (2013.01); *G01B 11/03* (2013.01); *G01B 11/24* (2013.01); *G01B 11/2408* (2013.01); *G01B 11/25* (2013.01); *G01B 11/303* (2013.01); *G01N 21/93* (2013.01); *G01N 21/95692* (2013.01); *G06T 7/001* (2013.01); *G06T 7/0002* (2013.01); *G06T 7/0004* (2013.01); *G06T 7/0008* (2013.01); *G06T 2207/10152* (2013.01); *G06T 2207/20081* (2013.01); *G06T 2207/30108* (2013.01); *G06T 2207/30164* (2013.01)

(58) Field of Classification Search
None
See application file for complete search history.

(56) References Cited

U.S. PATENT DOCUMENTS

| | | | |
|---|---|---|---|
| 5,003,615 A * | 3/1991 | Seitz | 382/108 |
| 5,125,035 A | 6/1992 | McCarthy et al. | |
| 6,268,572 B1 * | 7/2001 | Wilson, Jr. | 177/126 |

(Continued)

*Primary Examiner* — Anner Holder
*Assistant Examiner* — Ellyar Y Barazesh
(74) *Attorney, Agent, or Firm* — Miller, Matthias & Hull LLP

(57) ABSTRACT

A calibration artifact for an inspection system is provided. The calibration artifact comprises a base adapted for placement within a holding fixture of an inspection system during calibration, a sphere operatively connected to the base, and a light source operatively connected to the base. The base, the sphere, and the light source are removable from the inspection system after calibration.

20 Claims, 6 Drawing Sheets

(56) References Cited

U.S. PATENT DOCUMENTS

| | | | |
|---|---|---|---|
| 6,489,989 B1* | 12/2002 | Shapiro et al. | 348/180 |
| 2003/0231793 A1* | 12/2003 | Crampton | 382/154 |
| 2004/0223053 A1* | 11/2004 | Gladnick et al. | 348/79 |
| 2007/0043526 A1* | 2/2007 | De Jonge et al. | 702/94 |
| 2007/0276629 A1 | 11/2007 | Koonankeil | |
| 2008/0055205 A1* | 3/2008 | Chung et al. | 345/76 |
| 2009/0185027 A1* | 7/2009 | Cox et al. | 348/36 |
| 2011/0025853 A1* | 2/2011 | Richardson | 348/159 |

* cited by examiner

MACHINE TOOL—BASED, OPTICAL COORDINATE MEASURING MACHINE CALIBRATION DEVICE

CROSS-REFERENCE TO RELATED APPLICATION

This application is a continuation in part of U.S. patent application Ser. No. 12/772,510, filed on May 3, 2010, which is incorporated herein by reference.

FIELD OF THE DISCLOSURE

This disclosure relates generally to systems and methods for inspecting manufactured articles and, more particularly, to a calibration device for these inspection systems.

BACKGROUND OF THE DISCLOSURE

Gas turbine engines, such as those used to power modern aircraft, include a compressor for pressurizing a supply of air, a combustor for burning fuel in the presence of high pressurize, compressed air to generate and accelerate high temperature, high velocity combustion gases, and a turbine for extracting energy from the resultant combustion gases. The combustion gases leaving the turbine are exhausted through a nozzle to produce thrust to power the aircraft. In passing through the turbine, the combustion gases turn the turbine, which turns a shaft in common with the compressor to drive the compressor.

As the hot combustion gases pass through the turbine, various turbine elements, such as the turbine stator vanes and turbine rotor blades of the turbine, are exposed to hot combustion gases. In order to protect these turbine elements from exposure to the hot combustion gases, it is known to cool the turbine blades and vanes. In order to facilitate cooling of the blades and vanes, it is known to form the turbine blades and vanes with complex systems of internal cooling passages into which compressor bleed air, or another cooling fluid, is directed to cool the blade or vane. The cooling air exits the blade/vane through a system of holes arranged in such a manner that the exterior surface of the blade/vane is cooled, and is then passed out of the engine with the rest of the exhausted combustion gases.

In some turbine blade/vane embodiments, the cooling air exit holes are arranged in a specific pattern on various facets of the blade/vane airfoil to create a surface cooling film. The surface cooling film creates a layer of cool air, which insulates the airfoil from the hot combustion gases passing through the turbine. In order to ensure that the surface cooling film properly forms, various shaped exit holes are precisely located and bored at various angles on the surface of the airfoil. Thus, after manufacture it is necessary to inspect the blades and vanes to ensure the holes are properly positioned.

Conventional inspection systems include a fixture for holding the turbine blade/vane being inspected, a video camera, and a computer for controlling the inspection process and processing the video camera images. Generally, conventional inspection systems require inspection of each cooling hole from a gun-barrel view, which typically also requires the use of a five-axis coordinate measuring machine (CMM) for orientating the element and stepping the video probe from hole to hole. The turbine vanes and blades may, for example, have as many as 200 to over 300 cooling holes, each of which must be individually inspected.

Conventional inspection systems implement a step and stop process inspection, wherein the video camera is moved from hole location to hole location and positioned in a stationary relationship relative to the hole for a period of about 1.5 to 2.0 seconds before moving on to the next hole. This dwell time is needed for the video camera and the target hole to synchronize position, for the video camera to image the target hole, and the computer to analyze the dimensional measurements and output results. The video camera has a low frame rate capability, typically only 30 frames per second. Typically, inspection of a single airfoil may take as long as ten minutes, depending upon the number of holes and also the time required in initial part probing. Part probing is required to properly position the part to be inspected in the workpiece fixture prior to initiating the actual hole inspection, which in conventional practice can take from about 1.5 minutes to over 3 minutes.

Conventional calibration techniques for inspections systems include using two separate artifacts to measure all of the calibration parameters. In addition, those calibration artifacts require a dedicated, fixed location of the machine table and a hardwired connection to a power source. Use of a dedicated location to the side of the main work area requires extra reach for at least one of the machine axes. As a result, motors, actuators, bearings and scales are longer, the machine is heavier, and more space is needed solely to accommodate for calibration. Along with the added installation expense, there are reliability costs and safety concerns associated with the wires routed through the articulating joints of the machine, electrical contacts and grounding. Therefore, there is a need for a simplified and more reliable calibration system. This disclosure is directed to solving this need and provides a way to reduce the cost and complexity of a calibration device for inspection systems.

SUMMARY OF THE DISCLOSURE

According to one embodiment of the present disclosure, a calibration artifact for an inspection system is disclosed. The calibration artifact may comprise a base adapted for placement within a holding fixture of an inspection system during calibration, a sphere operatively connected to the base, and a light source operatively connected to the base, the base, the sphere, and the light source being removable from the inspection system after calibration.

According to another embodiment, a calibration system is disclosed. The calibration system may comprise a self-contained calibration artifact and an inspection system. The calibration artifact may comprise a base, a sphere, and a light source. The calibration artifact may be adapted for placement within the inspection system during calibration and can be removed thereafter.

According to yet another embodiment, a method for calibrating an inspection system is disclosed. The method may comprise providing an inspection system with a holding fixture and providing a self-contained calibration artifact with a sphere, a light source, and a base adapted for placement within the inspection system during calibration. The method may further comprise placing the calibration artifact within the holding fixture of the inspection system, using the inspection system to measure a set of parameters based on the calibration artifact, and removing the calibration artifact from the holding fixture of the inspection system.

BRIEF DESCRIPTION OF THE DRAWINGS

For a further understanding of the disclosure, reference will be made to the following detailed description which is to be read in connection with the accompanying drawing, where.

DETAILED DESCRIPTION OF THE DISCLOSURE

Figure 1:
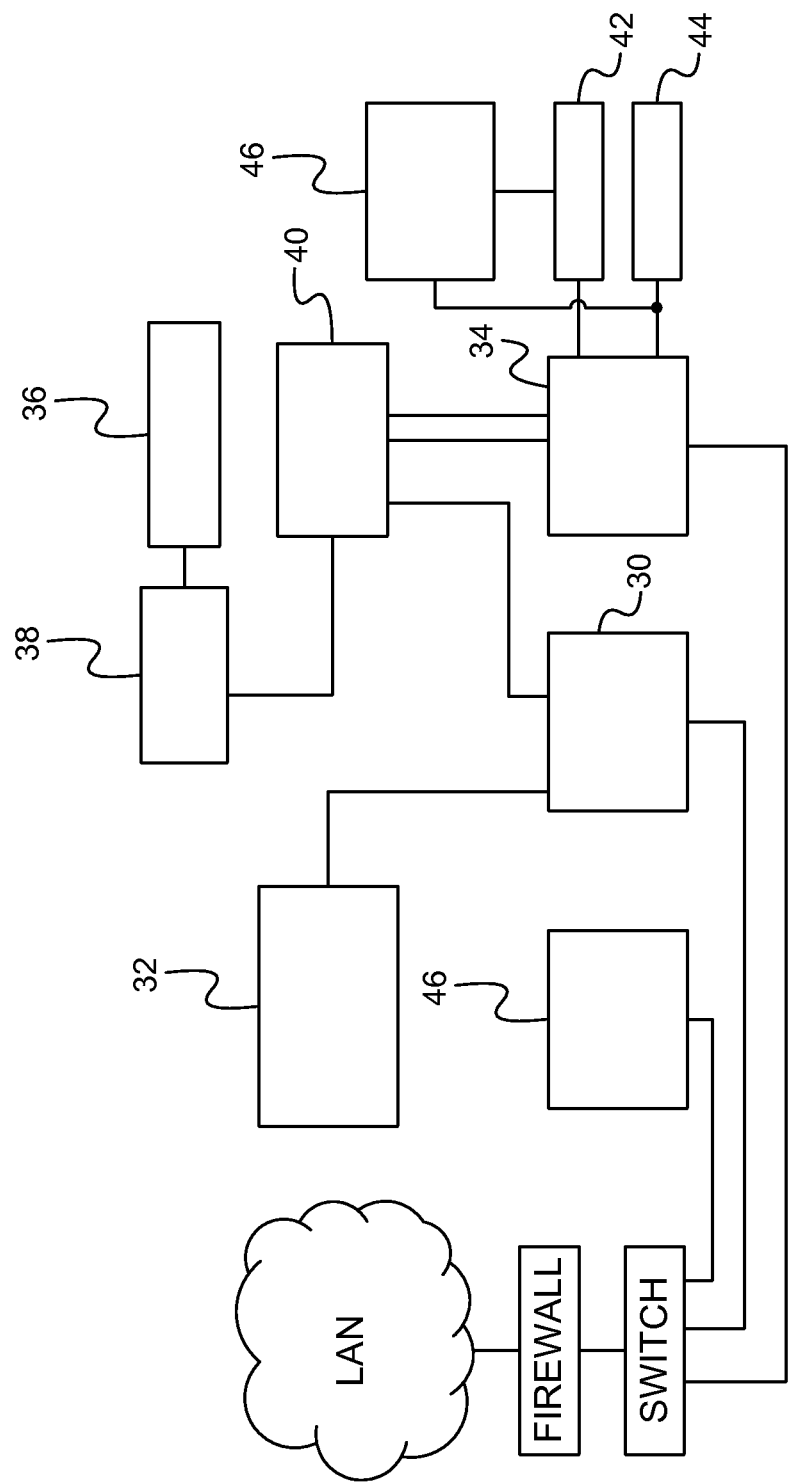
FIG. 1 is a block diagram schematic illustrating an exemplary embodiment of an inspection system for on-the-fly inspection of a plurality of target features associated with a part to be inspected.

There is depicted schematically in FIG. 1 an exemplary embodiment of an inspection system 20 for quickly and accurately locating the position of multiple target features associated with an object to be inspected. For example, the inspection system 20 disclosed herein may be used and the method of inspecting disclosed herein implemented in connection with the inspection of a turbine airfoil 22, such as a turbine blade or vane shown in FIG. 2, for the purpose of verifying the actual location of each of a multiplicity of cooling air exit holes 24 opening on the surface 26 of the turbine airfoil 22. It is to be understood, however, that the inspection system and the method for inspecting disclosed herein may be adapted for locating other features on other objects.

Referring now to FIG. 1, the inspection system 20 includes a fixture 28 for holding the target part (not shown in FIG. 1) being inspected, a fixture position manipulator 30, a controller 32, a processor 34, a light array 36, a light array driver 38 and a high speed camera 40. The holding fixture 28 secures the target part to be inspected in a specific position relative to the holding fixture such that each part in a series of similar parts to be inspected is held in substantially the same position within the holding fixture 28 from part to part. The holding fixture 28 is secured to the fixture position manipulator 30 in a fixed position. The light array 36 is operatively associated with the high speed camera 40 and positioned for providing light on the target part to facilitate imaging of the part by the high speed camera 40. The light array driver 38 is operatively associated with the light array 36 for powering the light array 36 to illuminate the target part. The controller 32 is operatively associated with the fixture position manipulator 30 for commanding the fixture position manipulator 30 to selectively position the holding fixture 28 to orient the target part whereby the selected target feature to be imaged is in a desired orientation relative to the high speed camera 40. The controller 32 also controls positioning of the high speed camera 40 and coordinates the triggering of the high speed camera 40 with the orientation of the target feature such that the high speed camera 40 is triggered and the target feature imaged when the high speed camera is in a gun barrel shot position with respect to the selected target feature. By gun barrel shot position/alignment, it is meant that the focal point of the high speed camera 40 is aligned along a line extending normal to the surface of the target object at the location of the target feature to be imaged.

The inspection system 20 is capable of implementing an on-the-fly inspection process in accord with the method disclosed herein. In operation, the controller 32 controls positioning of the target part by manipulation of the fixture position manipulator 30 in a controlled coordinated manner with movement of the high speed camera 40 whereby continuous relative movement along a specified, arbitrary three-dimensional path over the plurality of selected target features to be imaged is maintained between the high speed camera 40 and the target part as the multiplicity of target features are imaged without pause. That is, the high speed camera does not stop and dwell over any target feature location during imaging of that location on the target part. Rather, in accord with the process disclosed herein, the high speed camera 40 and the selected target feature to be imaged are in relative motion at a constant speed as the high speed camera is triggered and images the selected target feature. By eliminating the dwell time over the part at each inspection site, the inspection time associated with inspecting an individual target feature, such as a cooling air hole on a turbine airfoil, is significantly reduced relative to the conventional step and stop inspection method.

In on-the-fly inspection as disclosed herein, the movement of the target feature of interest relative to the high speed camera 40 over the duration of the frame capture must be less than a reasonable fraction, such as for example $1/10^{th}$, of the true position tolerance of the target feature. Thus, in implementing the on-the-fly inspection method disclosed herein, the speed of movement of the high speed camera 40 is primarily limited by the frame rate capability, of the camera 40 and the ability of the high speed camera 40 to collect enough light during the exposure duration for adequate contrast so that the image of the target feature can be resolved. Generally, the high speed camera 40 should have an exposure duration, i.e. time required for imaging a target feature, of less than three (3) milliseconds. For example, a high speed camera having a frame rate capability of at least about 300 frames per second would enable imaging with relative motion between the camera and the target feature at a constant speed of at least about 50 inches per minute.

The light array 36 is provided for illuminating the target feature with sufficient light at least during the exposure duration, that is at the time the high speed camera 40 images the target feature. The light array 36 comprises a plurality of high intensity light emitting devices, for example light emitting diodes (LEDs), arranged to illuminate the target feature to provide adequate contrast. The number of light emitting diodes comprising the light array 36 depends upon the power level applied to drive each diode. If a higher power level is applied per diode, for example about one watt or more per diode, the number of light emitting diodes may be decreased. Conversely, if a lower drive power level per diode is desired, a greater number of light emitting diodes may be provided. However, conventional low power, i.e. low wattage, LEDs commonly used in commercial applications do not provide sufficient light output per diode to be used in implementing the on-the-fly inspection method disclosed herein. The number of LEDs may also be reduced if a means of focusing is provided in association with the light emitting devices forming the light array 36 to increase the flux (intensity per unit area) in the image field of view of the high speed camera 40. The LEDs making up the light array 36 may be arranged in a ring pattern, in a single row, a double row or any other suitable arrangement.

The light array driver 38 is controlled by the controller 30 through the high speed camera 40 to power the light emitting devices comprising the light array 36. Although the light array could be powered continuously during the inspection process, doing so creates excess heat and shortens the life of the lights. In implementing the method disclosed herein using a high speed camera, the light array 36 may be powered in synchronization with the imaging of the target feature by the high speed camera 40. When the high speed camera 40 is moving over the target feature, the high speed camera 40 triggers the light driver 38 to power the light array 36 to illuminate the target feature during the exposure duration. With LEDs making up the light array 36, the light driver 38 comprises a LED driver having the capability of selectively switching the light array LEDs from zero power to at least full power in less than one microsecond to flash the LEDs in coordination with the camera exposure duration. Precise coordination of the camera exposure duration and the LED flash duration is particularly important at the higher relative speeds of movement between the high speed camera 40 and the target feature to be imaged that may be used in implementing the on-the-fly inspection method disclosed herein to eliminate blurring and ensure clarity of the image of the target feature.

Additionally, the LED driver can have the capability of over-powering the light array LEDs, that is powering individual LEDs of the light array 36, all or selected LEDs thereof, at a power level in excess of the full rated power of the LED. Although over-powering the LEDs is not required when implementing the on the-fly inspection method disclosed herein, over-powering the LEDs produces a "strobing-like" effect that may improve image contrast and clarity during the exposure duration. This effect is not possible to attain with conventional lights, such as incandescent or halogen lights. The light array LEDs are arranged such that directional control is available for adjustment of the geometry comprising the orientation of the optical axis of the camera lens, the light from the LEDs, and the target part orientation surrounding the feature of interest. Adjustment may be achieved by selectively controlling, through software control, the intensity of each available light array LED at its respective location with respect to the target feature.

As noted previously, conventional step and stop inspection systems typically employ a 5-axis, coordinate measurement machine in combination with a low speed video camera. Such machines can move the video camera and/or the part to a location and orientation very well in a step and stop inspection process even though each axis may arrive at its individual target location at a different time. However, conventional coordinated measurement machines do not have the ability to control three linear and two rotary axes in a coordinated fashion for imaging while in motion as required in implementation of the on-the-fly inspection method disclosed.

In the on-the-fly inspection system 20, the fixture position manipulator 32 comprises a computer numerically controlled (CNC) machine under direct control of the controller 30. The CNC machine 32 secures the fixture 28 that holds the target object to be inspected. The CNC machine 32, under the control of the controller 30, provides coordinated five degree of freedom motion control for maneuvering the fixture 28 in the CNC machine 32 to align the target object to a desired orientation with the high speed camera 40 for imaging of the selected target feature. CNC machines with coordinated 5-axis motion control are known for use in the aerospace industry for machining applications, for example where the location and orientation of a cutting tool relative to the workpiece is important at all times when the two are in contact. However, the use of CNC machines with coordinated five degrees of freedom motion control is novel in inspection applications for imaging a target feature on a target object with a high speed camera while in relative motion along a three-dimensional path without the stop and step required in practice.

As noted above, in on-the-fly inspection as disclosed herein, the high speed camera 40 images the target feature while in relative motion with respect to the selected target feature at a constant speed. Depending upon the relative speed and the spacing between target features, the high speed camera 40 may be imaging several target features a second. Therefore, the inspection system must be capable of handling the images produced in such a manner as to not adversely impact control loop cycle time of the controller 30. During a single control loop cycle, the computer 34 will receive a signal from feedback devices of each axis as the actual position, modify this position of each axis with any active corrections as applicable, compare the result to the commanded position at that time, and output power signals to each axis motion control device (usually a motor) associated with the fixture position manipulator 32 subject to the various control parameters (tuning) which have been set. The control loop cycle time should desirably be around 1 millisecond or less. Performing analysis of images and performing other output functions during the "random" cycles when the images are available (1 in 150 cycles for example) in such a way that the cycle time can be maintained reliably would severely limit what the cycle time could be achieved and consequently severely limit the speed of measurements.

Accordingly, the inspection system 20 incorporates a parallel processor 34 for performing image analysis. Whenever the high speed camera 40 images a target feature, the single frame image is captured by the high speed camera 40 and stored to memory as a file in data archive 42. The processor 34 will access the image file, read the image file, analyze the image, determine the location of the target feature, for a hole center, and create the output data while the high speed camera and target object are in motion to align on the next target feature of interest. In conventional stop and step inspection methods, the image analysis was performed while the video camera remained stationary in front of the imaged target feature. In the on-the-fly inspection method disclosed herein, the image analysis occurs while the high speed camera and the target object are in relative motion along a three-dimensional path at its constant speed as the next target feature is brought into a gun shot barrel align with the high speed camera. Therefore, image analysis does not adversely impact control loop cycle time. If desired, an additional processor 46 may be provided in parallel with the processor 34 to assist in processing the images. Each of the processors 34 and 46, as well as the controller 30, may be commercially available microprocessors, each of which is typically associated with a separate computer monitor, memory bank and peripherals, but two or more of which may be associated with a common computer monitor, memory bank and peripherals, if practical from a logistics and processing viewpoint.

Figure 2:
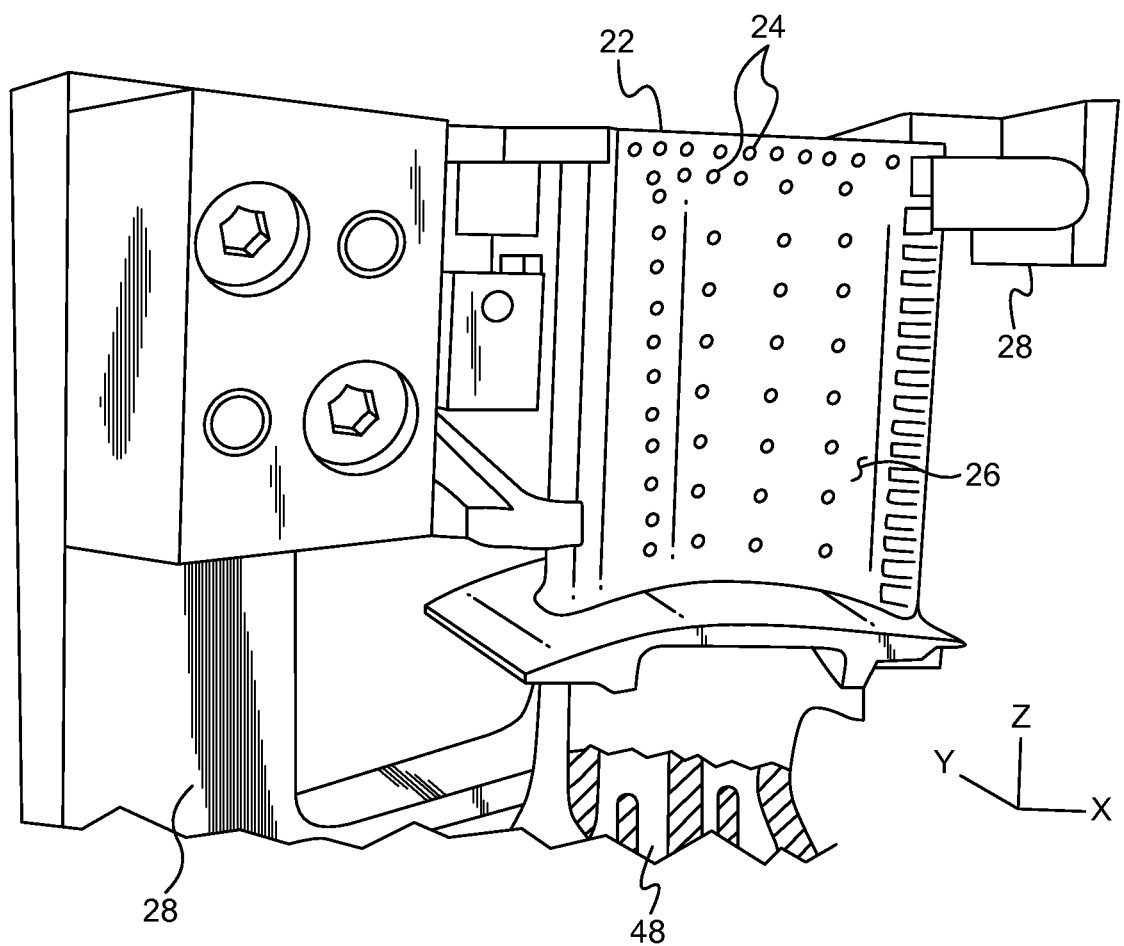
FIG. 2 is a partially cut-away elevation view of the pressure side of a turbine having a multiplicity of cooling air holes.

The on-the-fly inspection method will be described further as implemented for the inspection of turbine airfoils for the purpose of verifying the position of a multiplicity of cooling air holes. Referring to FIG. 2. there is depicted an exemplary embodiment of a turbine airfoil 22 having a multiplicity of cooling air exit holes 24 arranged in a generally column and row fashion on the pressure side surface 26 of the airfoil 22. The root or bottom of the airfoil 22 is shown in cut-away to reveal cooling air passages 48. To cool the turbine airfoils during operation of the gas turbine engine, high pressure air, typically compressor bleed air, enters the cooling passages 48, which extend into the interior of the turbine airfoil 22. At least a portion of the cooling air exits from the cooling air passages 48 through the cooling air exit holes 24 to flow along the exterior surface of the turbine airfoil 22. The multiplicity of cooling air exit holes 24 must be arranged in a precise pattern designed to achieve complete cooling coverage of the surface of the turbine airfoil 22. In an exemplary embodiment of a turbine airfoil, over 300 cooling air exit holes 24 may be provided with the cooling air exit holes 24 typically having a diameter of about 300 microns and typically being spaced apart at about 0.200 inches.

The on-the-fly inspection method disclosed herein can be used for verifying the precise actual location of each cooling air exit hole 24 on the turbine airfoil 22. To begin, through the user interface 50, which may be a dedicated computer terminal or a computer terminal in a network system, the operator selects the appropriate program for the turbine airfoil (blade or vane) to be inspected from a list of available part programs. The airfoil to be inspected, for example turbine airfoil 22, is loaded in a known manner in the fixture 28 of the fixture position manipulator 32, which in this implementation of the method comprises a five degree of freedom CNC machine. The high speed camera 40 and the holding fixture 28 are supported in the CNC machine 32 in spaced, facing relationship. The high speed camera 40 may be supported for movement in one or two linear degrees of freedom, while the holding fixture 28 is supported for movement in both rotational degrees of freedom and at least one linear degree of freedom. In a typical installation, the high speed camera 40 would be supported above the fixture and at least moveable along a vertical axis up and down relative to the turbine airfoil held in the holding fixture 28. With a turbine airfoil loaded onto the CNC machine 32, the location and orientation of the turbine airfoil with respect to each of the five degrees of freedom of the CNC machine 32 can be estimated based on the design of the holding fixture 28. As in conventional systems, the design of the holding fixture 28 includes the fixing of the turbine airfoil 22 to the holding fixture 28 in a repeatable consistent manner from airfoil to airfoil as well as the means of fixing the holding fixture 28 to the CNC machine 32 in a consistent manner.

It is possible, but not feasible, to know the location and orientation of the turbine airfoil with respect to the CNC machine to a level of accuracy required for the measurement of feature locations. This is due to the influence of variations that arise from actual dimensions of the turbine airfoil and holding fixture within their respective machining tolerances as well as the non-repeatability of airfoil loading and fixture loading. Because of the careful design and process controls that would be required to position the part deterministically to within the required limits, a touch-trigger probe is used to simply find the actual location and orientation of each individual turbine airfoil prior to its measurement. The part datum planes are established by measuring the location of 6 specific points on the surface of the turbine airfoil.

Figure 3:
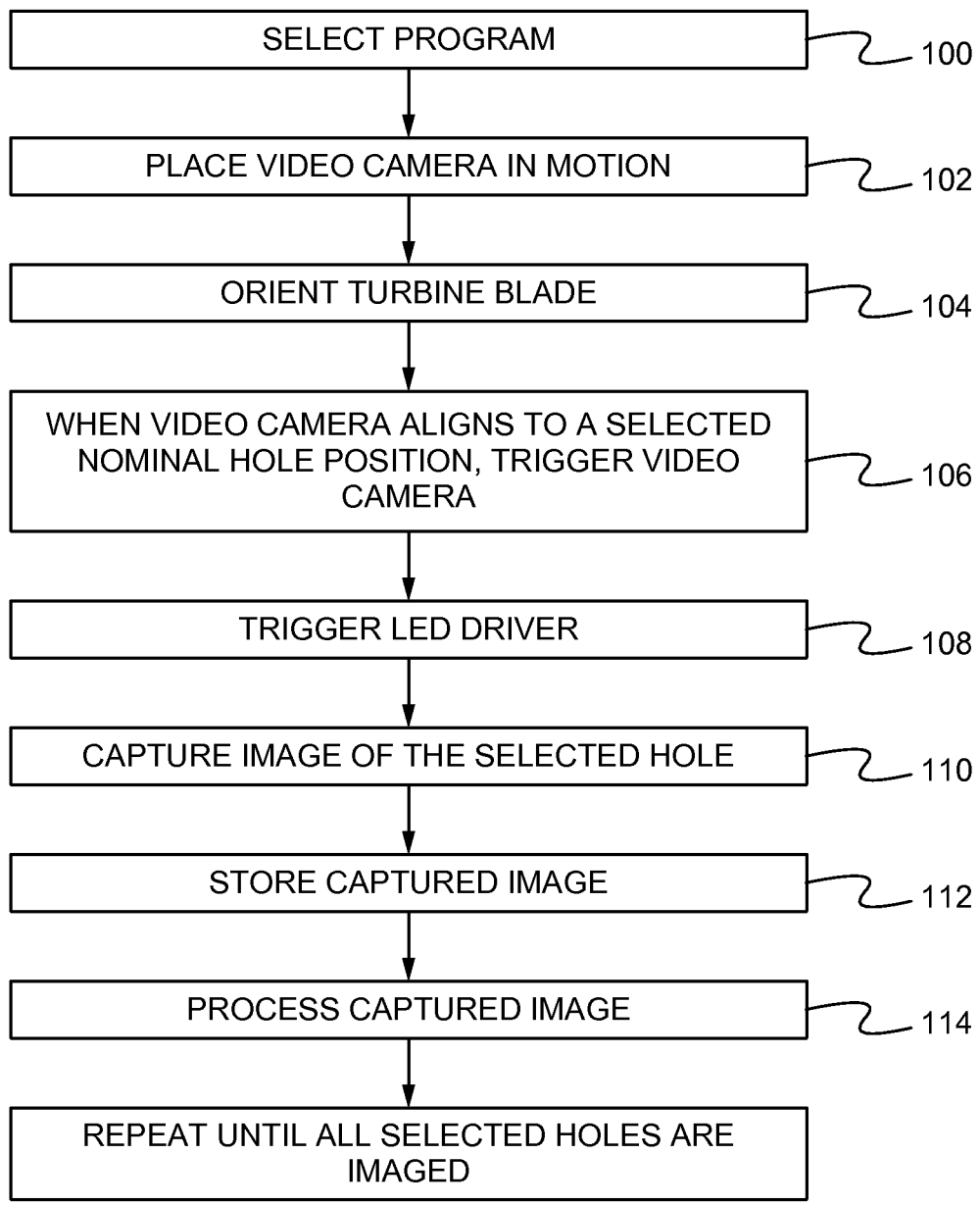
FIG. 3 is a flow chart illustrating a method for on-the-fly inspection in accord with an aspect of the invention.

Referring now to FIG. 3, when the operator selects the appropriate program associated with the turbine airfoil to be inspected, at step 100, the selected program will be loaded into the controller 30. The program will consist mainly as a list of positions for each of the 5 degrees of freedom associated with the CNC machine 32, i.e. 3 linear degrees of freedom (x, y and z coordinate axes) and two rotational degrees of freedom (one about the axis of the holding fixture and one in a plane orthogonal to the axis of the holding fixture). These positions correspond to the nominal locations of the holes to be inspected. The camera settings for the high speed camera 40, which in this implementation of the method disclosed herein comprises a video camera, are configurable by the data link with the controller 30. When a part program is selected, the controller 30 will make the previously specified settings on the video camera for that particular part program.

The actual inspection cycle begins with the computer 30, at step 102, placing the video camera 40 in motion and, simultaneously at step 104, maneuvering the fixture 28 holding the turbine airfoil. The video camera 40 and turbine airfoil are in relative motion along a three-dimensional path at a constant relative speed to orient the turbine airfoil and the video camera such that the next to be imaged target hole and the video camera are brought into gun barrel shot alignment. For example, the video camera and the turbine airfoil may be in relative motion along a three-dimensional path at a constant relative speed of at least about 50 inches per minute between holes in a row/column of holes 24 and at an even higher relative speed, for example about 200 inches per minute, between rows/columns of holes 24. The controller 30 controls the CNC machine 32 to maneuver the fixture 28 and relative movement of the video camera to properly orient the turbine airfoil 22 with respect to the video camera 40 for imaging of each individual hole 24 of the multiplicity of cooling air holes 24 on the surface of the turbine airfoil 22.

At step 106, at each instant during the inspection cycle that the video camera 40 aligns in gun barrel shot relationship to a nominal hole position, the controller 30 sends a signal to the video camera 40. At step 108, upon receipt of that signal from the controller 30, the video camera 40 triggers the LED driver 38 which in turn powers, that is switches from zero power to full power, the LEDs of the light array 36 for a preset duration. At step 110, in synchronization with the flashing of the LEDs of the light array 36, the video camera 40 captures an image of the target hole 22 as the video camera passes over the target hole.

At step 112, the captured image is stored in a designated folder in the data archive 42 associated with the processor 34. At step 114, the captured image is accessed and processed in parallel with the movement of the video camera 40 and the maneuvering of the fixture 28 while repositioning at a constant relative speed toward the next target hole. The basic result of an image analysis will be the pixel location of the centroid of the identified blob (Binary Large OBject), i.e. the cooling air exit hole 24. Based on previous calibration the location and rotation of the camera pixel array is known with respect to the machine coordinate system. Also, the location and orientation of the part coordinate system is known with respect to the machine coordinate system by the nominal tool design and by the results of the part probing which refines the tool matrix to actual. Furthermore, the location and orientation of each hole 24 is specified by the engineering definition for the part with respect to the part datum planes. Appropriate coordinate transformations are carried out by the processor 34 to determine the location of each hole 24 relative to that hole's nominal, specified location. The difference is the true position error.

The on-the-fly inspection method disclosed herein is capable of performing a hole location inspection of a turbine airfoil several times faster than the time required for using conventional step and stop hole inspection methods. For example, a turbine vane having 211 holes was subject to hole measurement inspection using a conventional step and stop method using a video camera having a frame rate capability of 30 frames per second. The time required to measure all of the 211 holes was timed at 443 seconds Implementing the on-the-fly method disclosed herein using a high speed video camera having a frame rate capability of 1000 frames per second and moving the video camera and maneuvering the orientation of the turbine airfoil at a constant relative speed of 50 inches per minute between holes in a row and at a speed of 200 inches per minute between rows, it is estimated the measurement time for measuring the same 211 holes would be reduced to 43 seconds, a ten-fold decrease. As a further example, a turbine airfoil having 330 holes was subject to hole measurement inspection using a conventional step and stop method using a video camera having a frame rate capability of 30 frames per second. The time required to measure all of the 330 holes was timed at 690 seconds. Implementing the on-the-fly method disclosed herein using a high speed video camera having a frame rate capability of 1000 frames per second and moving the video camera and maneuvering the orientation of the turbine airfoil at a constant relative speed of 50 inches per minute between holes in a row and at a speed of 200 inches per minute between rows, it is estimated the measurement time for measuring the same 330 holes would be reduced to 57 seconds, an over ten-fold decrease.

Figure 4:
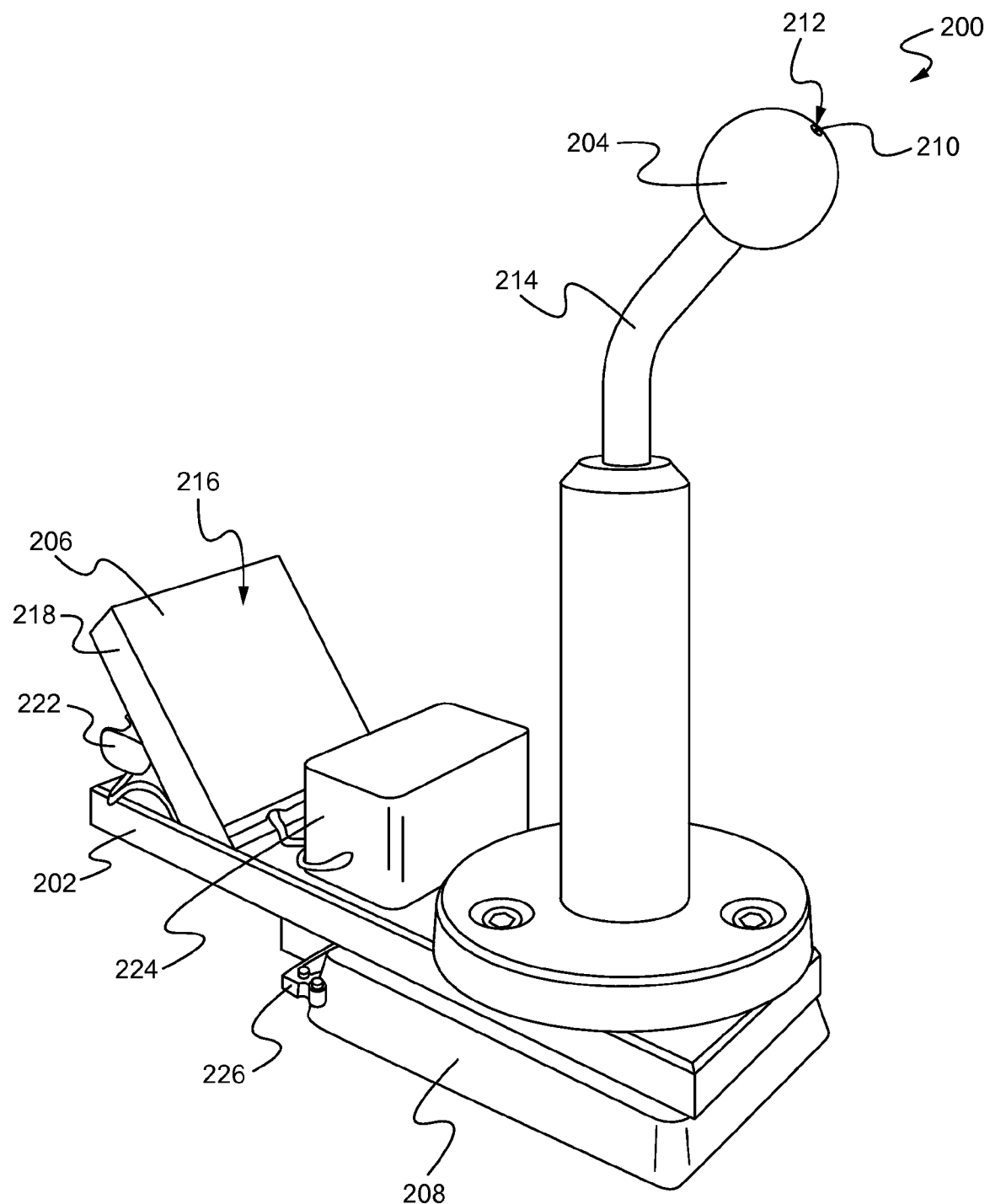
FIG. 4 is a perspective view of an inspection system calibration artifact made according to one embodiment of the present disclosure.
Figure 5:
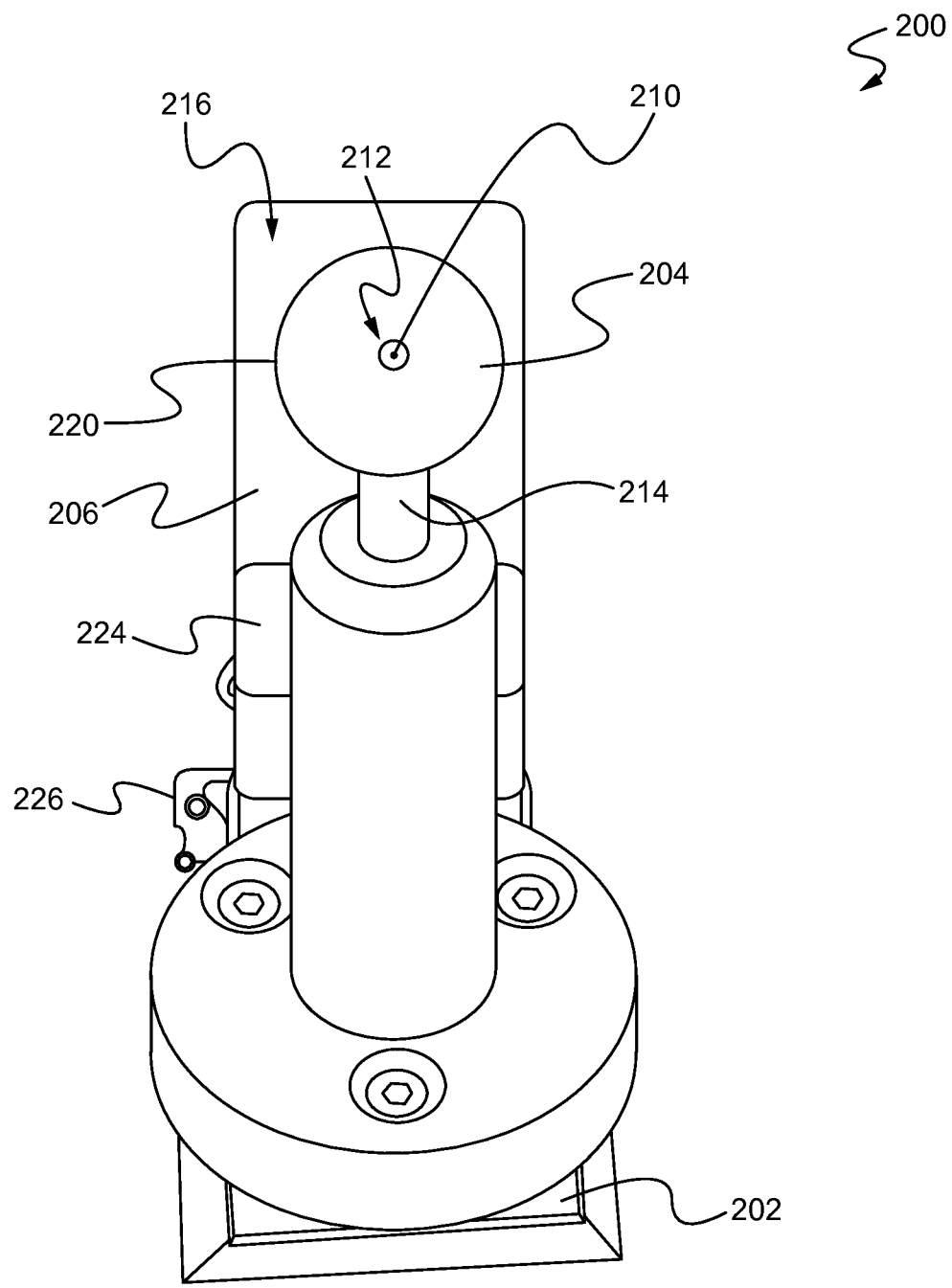
FIG. 5 is a top view of the calibration artifact from the position of the highspeed camera with the focal point of the sphere and the electroluminescent sheet of the calibration artifact normal to the camera axis of the highspeed camera.

Referring now to FIGS. 4 & 5, a calibration artifact 200 according to another embodiment of the present disclosure is shown. The calibration artifact 200 may be used to calibrate the inspection system before inspection and may comprise a base 202, a calibration sphere 204, and a light source 206. The base 202 may be adapted for placement within an inspection system during calibration. For example, the base 202 may include a receiver 208 that is adapted for placement within the holding fixture of the inspection system. The holding fixture, which secures the target part to be inspected, may secure the calibration artifact 200 in the same way and in the same position and location it secures a target part. After calibration is finished, the calibration artifact 200 may be removed from the holding fixture of the inspection system and the target part to be inspected may be placed within the holding fixture for inspection. In so doing, the calibration artifact 200 of the present disclosure does not require a dedicated, fixed location on the machine table.

The calibration sphere 204 of the calibration artifact 200 may include a focal point 210 for the inspection system. The focal point 210 may comprise a dot on the top 212 of the sphere 204. A forty-five degree (45°) stem 214 may connect the sphere 204 to the base 202. Other angles and means of connecting the sphere 204 to the base 202 are certainly possible. The light source 206 may illuminate the sphere 204 during calibration and may comprise a sheet 216 of electroluminescent material. Attached to the electroluminescent sheet 216, a plate 218 may serve as a platform for the electroluminescent sheet 216 and may be connected to the base 202 at a forty-five degree (45°) angle, although other angles are certainly possible as well. In this way, when the calibration artifact 200 is rotated by the machine axes such that the electroluminescent sheet 216 and focal point 210 of the sphere 204 is normal to the camera axis of the highspeed camera, the calibration sphere 204 is surrounded by the uniform intensity, diffuse light, as shown best in FIG. 5. In this view of the highspeed camera, the edge 220 of the sphere 204 is well defined and the sphere 204 appears black in contrast to the light source 206, thereby making the sphere 204 and focal point 210 an accurate target for calibration by the highspeed camera of the inspection system. Although shown and described as an electroluminescent sheet 216 with a platform plate 218 at a 45° angle to the base 202, it will be understood that any type of light source and mounting may be used to illuminate the sphere 204 on the calibration artifact 200.

To power the light source 206, the calibration artifact 200 may further comprise a self-contained power source, such as a battery 222 and a power adapter 224 both mounted to the base 202, as shown in FIG. 4. The light source 206 may be adapted to low current requirements. For exemplary purposes only, a small power adapter may use, including but not limited to, a nine volt (9V) battery to supply one hundred volts (100V) or one thousand hertz (1000 Hz) alternating current (AC) at very low amps to the light source 206. Other self-contained power sources are certainly possible. This results in a self-contained light source 206 on the calibration artifact 200 that does not require a hardwired connection to a power source outside of the calibration artifact 200.

The calibration artifact 200 may further include a switch 226 configured to turn on the light source 206 when the base 202 is placed within the inspection system during calibration. For example, the switch 226 may comprise a limit switch on the receiver 208 of the base 202. The limit switch automatically ensures that the light source 206 is on when the calibration artifact is loaded onto holding fixture of the inspection system and automatically ensures the light source 206 is off when the calibration artifact is taken out of the inspection system. In this way, the light source 206 would only be turned on during calibration and would be turned off when the calibration artifact 200 is not in use, thereby saving time and energy.

The inspection system may further include a software check (not shown) to ensure a light threshold exists on the calibration artifact for proper measurement during calibration. When the highspeed camera is targeting the sphere 204 of the calibration artifact 200 during calibration, the software of the inspection system may recognize that there is not enough light from the light source 206 if the edge 220 of the sphere 204 does not appear as a clear image. The software check may then produce an alert to the operator that the light threshold is not met or that the battery 222, the power adapter 224, or the electroluminescent sheet 216 of the light source 206 needs to be changed.

Figure 6:
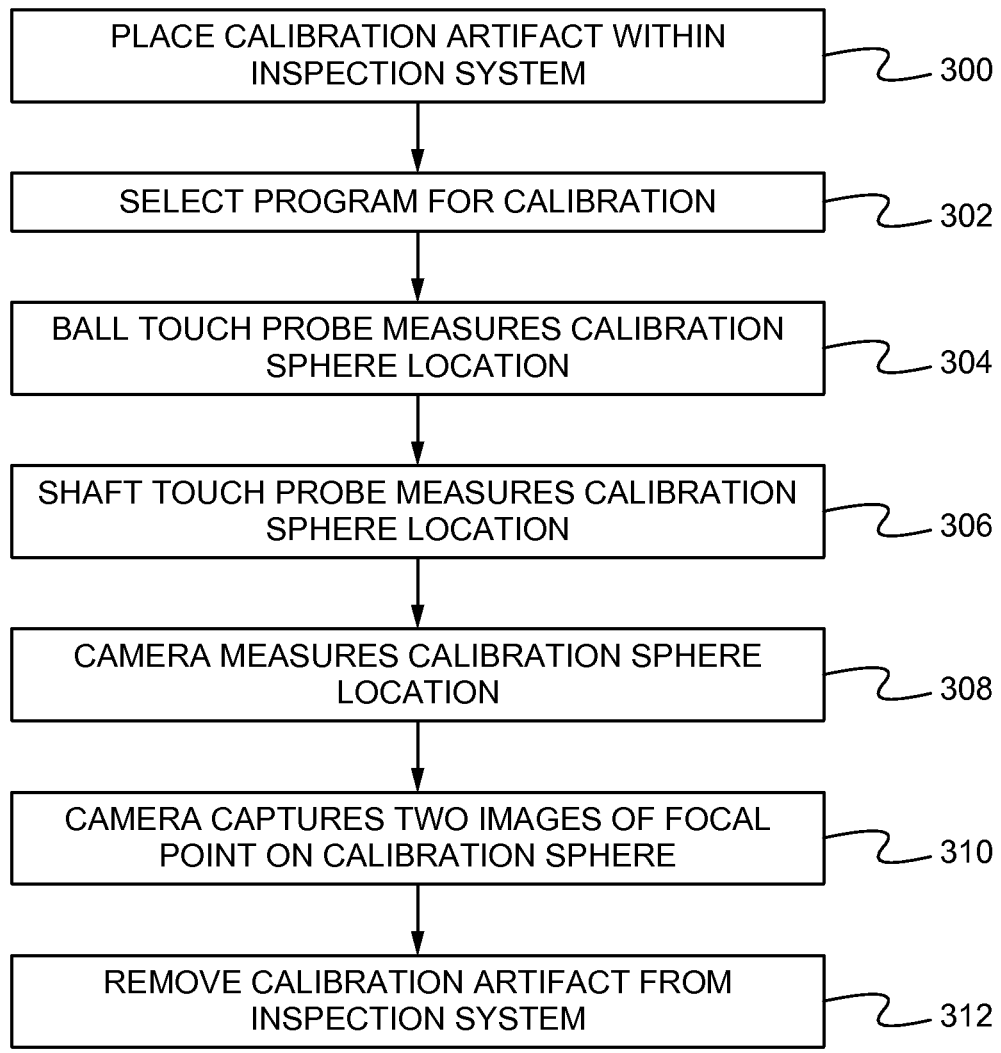
FIG. 6 is an exemplary flowchart outlining the steps of calibrating an inspection system using a calibration artifact of the present disclosure.

Referring to FIG. 6, in order to calibrate the inspection system, the operator places the calibration artifact on a workzone table or the like and loads the artifact onto the holding fixture of the inspection system, at step 300. The calibration artifact is loaded onto the same machine tool platform and in the same way as a target part to be inspected. At step 302, the operator selects the appropriate program to be loaded into the controller for calibration. During calibration, the touch probe, specifically the ball of the stylus and the shaft of the touch probe, and the highspeed camera have to be referenced to each other in x, y, and z machine coordinates. The highspeed camera rotation angle and the pixel scale factor also have to be calibrated.

Once the calibration artifact is loaded in the inspection system, the ball of the touch probe measures the location of the sphere of the calibration artifact in x, y, and z machine coordinates, at step 304. The center of the sphere is calculated based on the measurements taken by the ball of the touch probe and that value is stored in the computer. Next at step 306, the shaft of the touch probe measures the location of the sphere again based on the ball touch probe's measurements, which results in an x offset value, a y offset value, and a z offset value relative to the ball touch probe and shaft touch probe. Next at step 308, the camera measures the location of the sphere, focusing on the top of the sphere, a solid surface, and the edge of the sphere against the electroluminescent sheet to find the location in x, y, and z machine coordinates. This results in x, y, and z offset values relative to the camera and the ball touch probe. At this point, the touch probe and highspeed camera are referenced to each other.

By moving the machine, at the next step 310, the camera then focuses in on the focal point or dot on the top of the sphere to calibrate the pixel scale factor. This is done by capturing two images of the dot on the sphere, which can then be used to calculate inches per pixel. From the two images of the focal point taken, the camera rotation angle can also be calibrated relative to the x-axis of the machine. As a result, all calibration parameters for the inspection system can be measured in a single automated routine using only one calibration artifact. Although the x offset value, y offset value, z offset value, camera rotation angle, and pixel scale factor are the only parameters described herein, it will be understood that other calibration parameters may certainly be measured based on the calibration artifact of the present disclosure without departing from the spirit and scope of the invention. After calibration is finished, at step 312, the operator removes the calibration artifact from the holding fixture of the inspection system and a target part may subsequently be loaded to begin inspection.

From the foregoing, it can be seen that the present disclosure sets forth an improved calibration device for an inspection system. All calibration parameters can be measured from a single calibration artifact, and calibration can be accomplished in a single automated routine, thereby making the present disclosure a simplified and more efficient calibration device for inspection systems. In addition, the compact and self-contained assembly of the present disclosure does not require wires or electrical contacts connected to a power source outside of the calibration artifact. Nor does the compact and self-contained calibration artifact of the present disclosure require a dedicated, fixed location on the machine table. Moreover, by enabling the present calibration artifact to be loaded interchangeably in the inspection machine in the same way as a target part, the calibration artifact of the present disclosure not only provides a safe and reliable calibration device for an inspection system, but also does so in a cost effective and energy efficient manner.

The terminology used herein is for the purpose of description, not limitation. Specific structural and functional details disclosed herein are not to be interpreted as limiting, but merely as basis for teaching one skilled in the art to employ the present invention. Those skilled in the art will also recognize the equivalents that may be substituted for elements described with reference to the exemplary embodiments disclosed herein without departing from the scope of the present invention.

While the present invention has been particularly shown and described with reference to the exemplary embodiment as illustrated in the drawing, it will be recognized by those skilled in the art that various modifications may be made without departing from the spirit and scope of the invention. For example, in the implementation of the inspection method described herein, the inspection measures the hole location in two dimensions. However, in other applications, the method could be used to measure hole size or the orientation of the axis of the hole relative to the surface of the airfoil. Therefore, it is intended that the present disclosure not be limited to the particular embodiment(s) disclosed as, but that the disclosure will include all embodiments falling within the scope of the appended claims.

What is claimed is:

1. A calibration artifact for an inspection system comprising:
    a base adapted for placement within a holding fixture of an inspection system during calibration, the holding fixture configured to secure the base in a same manner and position as a target part is held within the holding fixture during actual inspection;
    a sphere operatively connected to the base; and
    a light source operatively connected to the base, the light source separate from the sphere and positioned to illuminate the sphere such that an edge of the sphere is clearly defined in contrast to the light source when targeted by a camera of the inspection system; the base, the sphere, and the light source configured to be removable from the inspection system after calibration.

2. The calibration artifact of claim 1, wherein the sphere includes a focal point for the inspection system.

3. The calibration artifact of claim 2, wherein the focal point of the sphere comprises a dot on the top of the sphere.

4. The calibration artifact of claim 1, wherein the light source is adapted to low current requirements.

5. The calibration artifact of claim 1, wherein the light source comprises an electroluminescent sheet.

6. The calibration artifact of claim 5, wherein the sphere is connected to the base by a forty-five degree (45°) stem, and the electroluminescent sheet is connected to the base at a forty-five degree (45°) angle.

7. The calibration artifact of claim 1, further comprising a self-contained power source.

8. The calibration artifact of claim 1, further comprising a battery and a power adapter.

9. The calibration artifact of claim 1, further comprising a switch configured to turn on the light source when the base is placed within the inspection system during calibration.

10. A calibration system comprising:
    a self-contained calibration artifact comprising a base, a sphere, and a light source separate from the sphere, the light source positioned to illuminate the sphere such that an edge of the sphere is clearly defined in contrast to the light source when targeted by a camera of the inspection system; and
    an inspection system, the calibration artifact adapted for placement within the inspection system during calibration and for removal thereafter, the inspection system configured to secure the calibration artifact in a same manner and position as a target part is held within the inspection system during actual inspection.

11. The calibration system of claim 10, wherein the inspection system includes a fixture for holding a target object.

12. The calibration system of claim 11, wherein the calibration artifact is adapted for placement within the holding fixture of the inspection system during calibration.

13. The calibration system of claim 10, wherein the light source is adapted to low current requirements.

14. The calibration system of claim 10, wherein the calibration artifact further comprises a self-contained power source.

15. The calibration system of claim 10, wherein the inspection system includes a software check to ensure a light threshold exists on the calibration artifact for proper measurement during calibration.

16. The calibration system of claim 15, wherein the software check alerts an operator of the inspection system if the light is not sufficient.

17. The calibration system of claim 10, wherein the inspection system can establish all calibration parameters measuring only the calibration artifact.

18. A method for calibrating an inspection system comprising:
    placing a self-contained calibration artifact within a holding fixture of the inspection system;
    holding the calibration artifact within the holding fixture in a same manner and position as a target part is held within the holding fixture during actual inspection;
    using the inspection system to measure a set of parameters based on the calibration artifact;
    illuminating a sphere of the calibration artifact with a light source of the calibration artifact such that an edge of the sphere is clearly defined in contrast to the light source when targeted by a camera of the inspection system; and removing the calibration artifact from the holding fixture of the inspection system.

19. The method of claim 18, wherein the set of calibration parameters comprises an x offset value, a y offset value, a z offset value, a camera rotation angle, and a pixel scale factor.

20. The method of claim 18, wherein the calibration artifact does not include wires or electrical contacts connected to an outside power source.

* * * * *